United States Patent [19]

Bollé

[11] Patent Number: 5,608,469
[45] Date of Patent: Mar. 4, 1997

[54] SUNGLASSES WITH REMOVABLE SIDE SHIELDS

[75] Inventor: Maurice J. G. Bollé, Oyonnax, France

[73] Assignee: Etablissements Bollé S.n.c., Oyonnax, France

[21] Appl. No.: 492,805

[22] Filed: Jun. 20, 1995

[51] Int. Cl.⁶ .............................. G02C 7/10; G02C 5/14
[52] U.S. Cl. ............................. 351/44; 351/121; 2/449
[58] Field of Search ................................. 351/111, 121,
351/41, 44, 45, 46, 47, 57, 58, 59, 158;
2/13, 451, 449, 440, 10, 12, 15

[56] References Cited

U.S. PATENT DOCUMENTS

| | | |
|---|---|---|
| 2,296,634 | 9/1942 | Fink . |
| 3,189,913 | 6/1965 | Hoffmaster . |
| 3,209,366 | 9/1965 | Lindblom . |
| 3,389,406 | 6/1968 | Mitchell . |
| 3,391,976 | 7/1968 | Lindblom . |
| 3,505,679 | 4/1970 | Bennett ........................... 2/13 |
| 3,721,490 | 3/1973 | Prince ............................. 2/13 |
| 4,674,851 | 6/1987 | Jannard . |
| 4,730,915 | 3/1988 | Jannard . |
| 4,801,199 | 1/1989 | Penora . |
| 4,810,080 | 3/1989 | Grendol et al. . |
| 4,834,525 | 5/1989 | Porche . |
| 5,032,017 | 7/1991 | Bolle . |
| 5,035,498 | 7/1991 | Bolle . |
| 5,359,370 | 10/1994 | Mugnier . |
| 5,387,949 | 2/1995 | Tackles . |
| 5,394,567 | 3/1995 | Vatterott ........................ 2/449 |
| 5,410,763 | 5/1995 | Mugnier . |
| 5,438,706 | 8/1995 | Lambur ........................... 2/13 |

FOREIGN PATENT DOCUMENTS 2395522  6/1977  France .

OTHER PUBLICATIONS

Bollé product catalogue, ©1993, Bollé America, Inc.
Bollé Protective Eyewear product catalogue, ©1991, Denver, Colorado.
Bollé product catalogue, ©1994, Bollé America, Inc.

Primary Examiner—William L. Sikes
Assistant Examiner—Hung Xuan Dang
Attorney, Agent, or Firm—Carol W. Burton; Gregg I. Anderson; Holland & Hart LLP

[57] ABSTRACT

Sunglasses (20) having side shields (28) for blocking the sun at their lateral edges, include lenses (22) joined by a frame or bridge (21), temples (24) hingedly joined to the frame, the side shields (28) being slidably mounted on the temples (24) adjacent the hinges (25). The side shields have spaced ribs (29) on their inner surface (51) defining a channel (30) for receiving a temple bar, with inwardly projecting lips (31) on the ribs for engaging and releasing the temple. The side shields can slide forward and off the temples when the temples are folded, and are securely held on the temples when the temples are open and in use.

13 Claims, 4 Drawing Sheets

SUNGLASSES WITH REMOVABLE SIDE SHIELDS

BACKGROUND OF THE INVENTION

1. Field of the Invention

The present invention relates to eyeglasses such as sunglasses.

2. Description of the Prior Art

Sunglasses with side shields to block light from entering the sides of the glasses are known in the art. Such side shields are commonly formed of opaque material such as plastic, and snap or are permanently formed on the frame or temples of the eyeglasses near the point at which the temples are hinged to or join the frame or bridge of the glasses.

OBJECTS OF THE INVENTION

The principal object of the present invention is to provide sunglasses having improved removable side shields.

Another object of the invention is to provide side shields of the foregoing character which remove easily, yet will not come off accidently while the glasses are in use.

Other objects and advantages will become apparent from the following description and accompanying drawings.

SUMMARY OF THE INVENTION

Sunglasses having shields embodying the present invention include lenses joined by a frame or bridge, ear pieces or temples hingedly joined to the frame, and shields which can slide on and off the temples when the temples are rotated inward toward each other. The shields are each formed as an integral body having inner and outer surfaces with two spaced apart temple engaging arms or ribs on the inner surface. The ribs further define inwardly projecting appendages or lips for sliding over and holding the side shields on the temples.

The temples are hingedly attached to the frame of the glasses with the outer hinge elements securely attached to the temples, the inner hinge elements securely attached to the frame, and a hinge connector such as a screw or pin joining the inner and outer hinge elements. Each outer hinge element is attached to or imbedded in an inner corner of the temple. The illustrated frame curves rearwardly and has an inner hinge element at each inner corner where it meets and is hinged to the temples. When the temple is rotated or swung outwardly, as when the glasses user is wearing the glasses, the outer end of the temple is flush with the outer edge surface of the curved back portion of the frame. When the temples are swung inwardly, as for storing the glasses in a case, the outer end surfaces of the temples rotate away from the outer surface of the back portion of the frame, leaving a gap between the temple end and the frame. The arms of the side shields can then slide over the temples at the gap. When the temples are folded outwardly, the side shields cannot slide forward, because the arms are blocked by the frame of the eyeglasses.

DESCRIPTION OF THE PREFERRED EMBODIMENT

Figure 1:
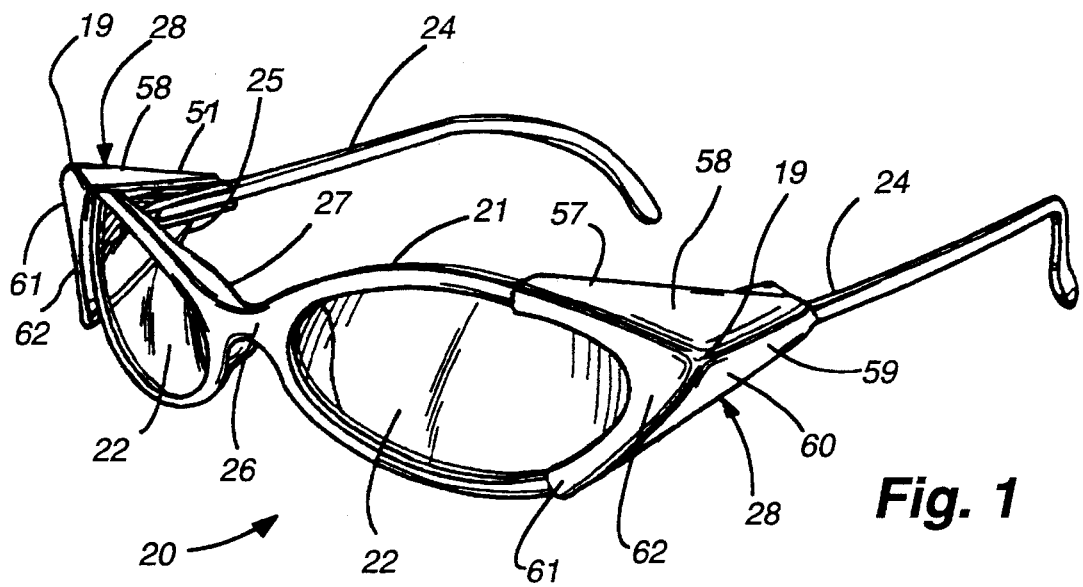
FIG. 1 is a front perspective view of sunglasses with shields embodying the present invention.

The present invention is embodied in sunglasses 20 formed by a frame or bridge 21 supporting lenses 22 (FIGS. 1–4). Ear pieces or temples 24 are secured by hinges 25 to the frame 21 at opposite sides thereof, and a central nosepiece 26 is integrally formed on the frame between the lenses 22 and defines nosepads 27. In accordance with the invention, shields 28 are releasably secured to and supported on the temples 24 in a position to cover and shield the area of the sunglasses around and laterally of the temple hinges 25.

Figure 5:
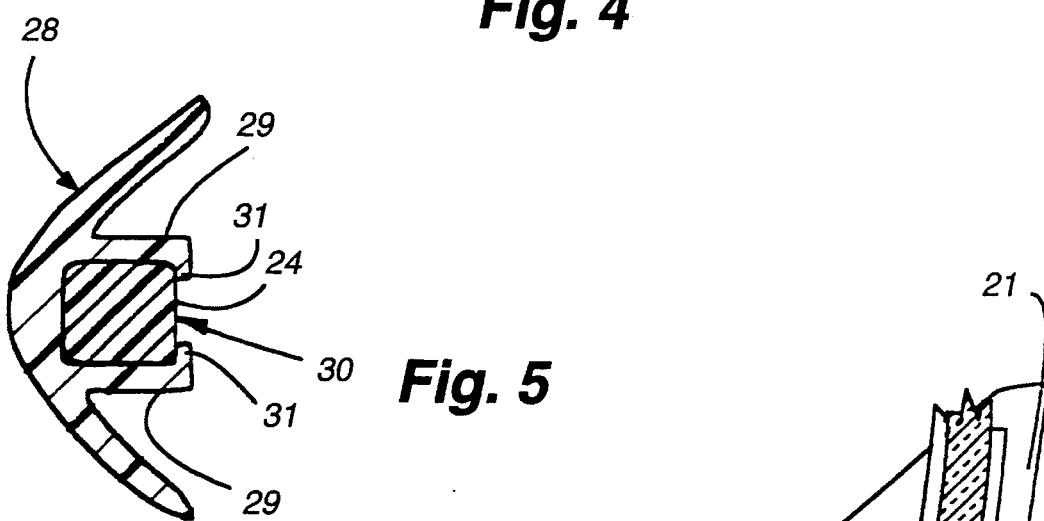
FIG. 5 is an enlarged section view taken substantially in the plane of line 5—5 on FIG. 3.

Each shield 28 is formed as an integral body of a moldable or shapable material such as plastic, and defines on its inner surface a pair of spaced elongated stiffly resilient ribs 29, forming a temple receiving channel 30. For gripping the temples and releasably securing the shield thereto, the spaced ribs 29 straddle the temple shaft and inturned flanges or lips 31 on the outer edges of the arms 29 releasably engage the temple 24 and hold the shield 28 securely thereon (FIG. 5). To this end, the ribs 29 slide over a temple 24 with the projections or lips 31 engaging the back surface of the temple 24 to prevent the shield 26 from pulling sidewise off the temple 24.

Figure 6:
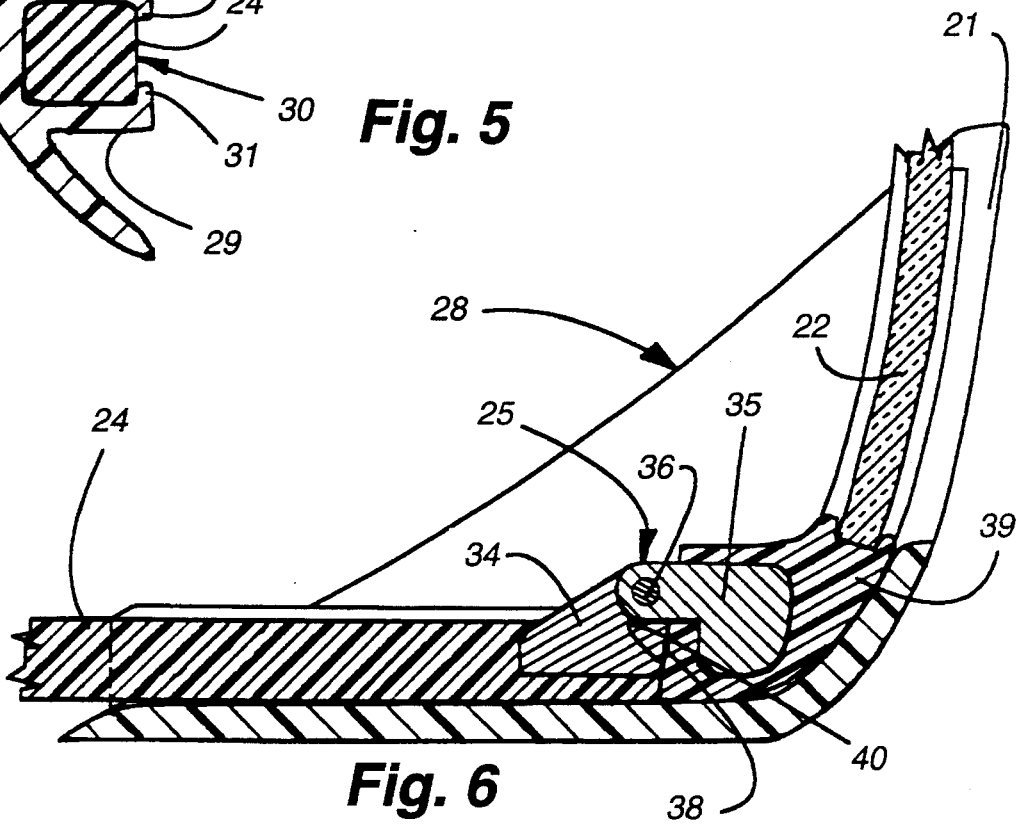
FIG. 6 is an enlarged section view taken substantially in the plane of line 6—6 on FIG. 3.
Figure 8:
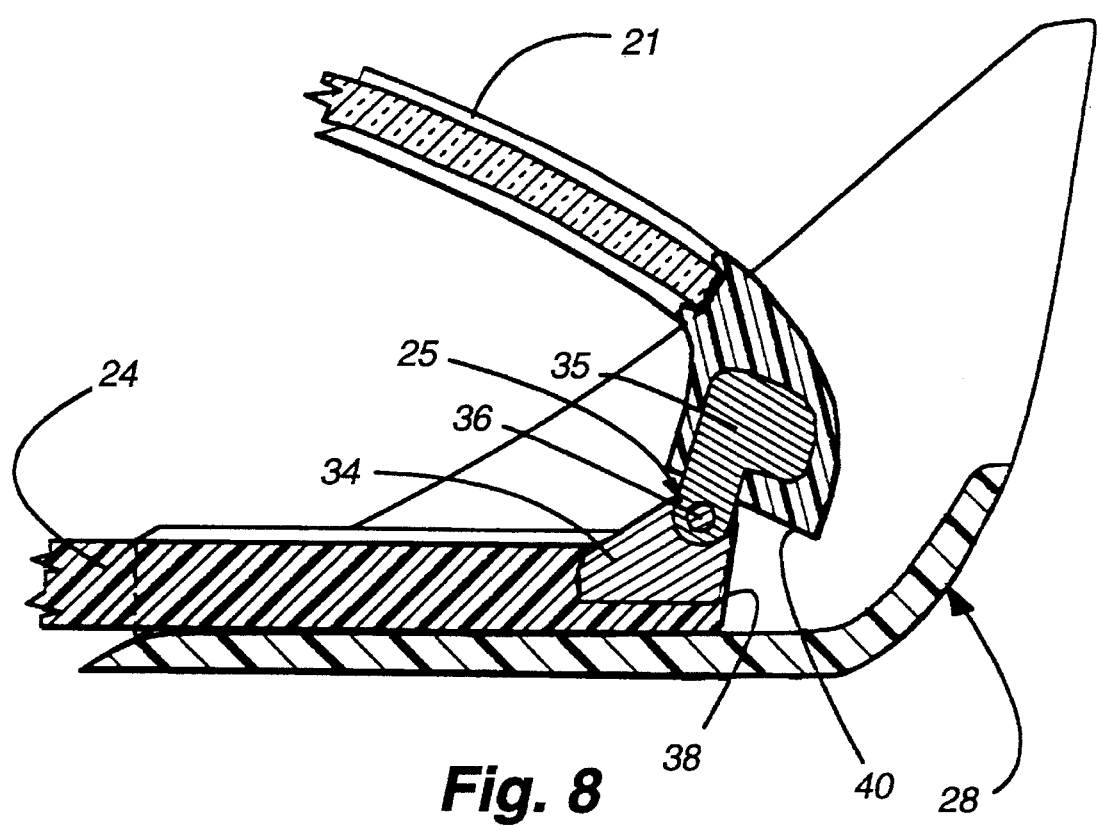
FIG. 8 is a section view similar to FIG. 6 but with a temple partially folded as shown in FIG. 7.
Figure 7:
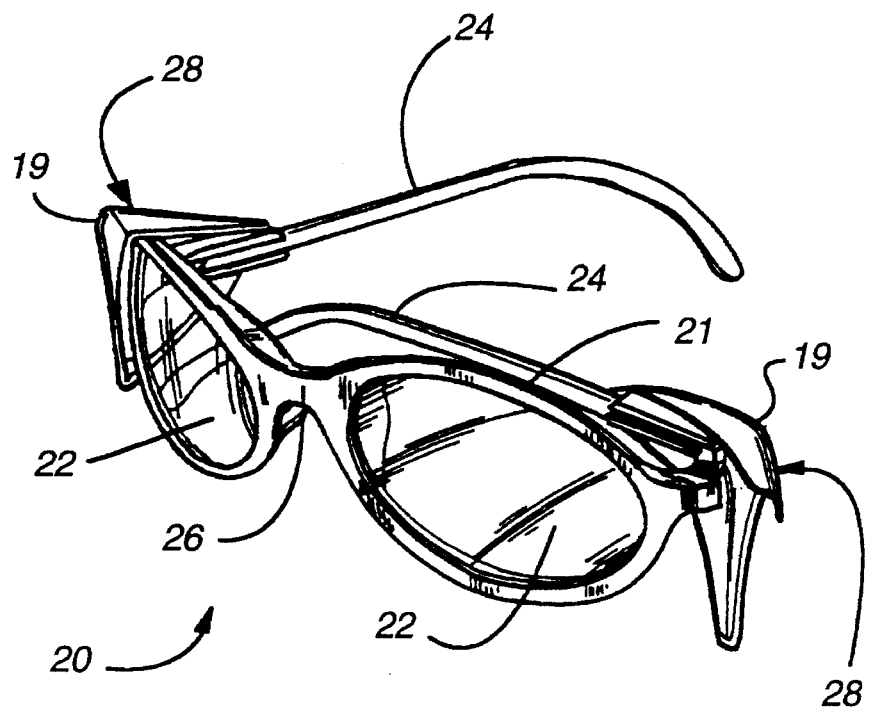
FIG. 7 is a perspective view similar to FIG. 1 but showing the eyeglasses with a temple partially folded.

The shield 28 is received in the channel 30 and readily slides on and off the temple 24 as shown in FIGS. 6 and 7. Each temple 24 is attached to the frame 21 by a hinge 25. The hinge is formed by a temple hinge element 34 securely attached to one end of a temple 24 and a frame hinge element 35 securely attached to the frame 21, a pivot pin or screw 36 hingedly joining them. The temple hinge element 34 is mounted on and partially embedded in a temple 24 and extends laterally therefrom, as shown in FIGS. 6 and 7, leaving the end 38 of the temple 24 exposed. The frame hinge element 35 is mounted on and partially embedded in a rearwardly extending enlargement or hinge boss 39 integrally formed on the frame 21 as shown in FIG. 6. The hinge boss 39 defines a rearwardly facing surface 40. When the temple 24 is rotated or swung outwardly as shown in FIG. 6, the outer end surface 38 of the temple 24 abuts the rearwardly facing surface 40 of the frame 21 as shown in FIG. 6.

When temple 24 is folded or swung inwardly toward the frame 21, as shown in FIG. 7, the outer end surface 38 of temple 24 swings away from the outer rear surface 40 on the frame 21 and is exposed, leaving a gap between the outer end surface 38 of the temple and the rear surface 40 of the frame 21. With the temple 24 in this position, the arms 16 of the side shield can slide forward over temple 24 at the gap. When the temple 24 is opened, as shown in FIG. 6, the side shield cannot slide forward because the curved back of frame 21 blocks the ribs of shield 15.

Figure 2:
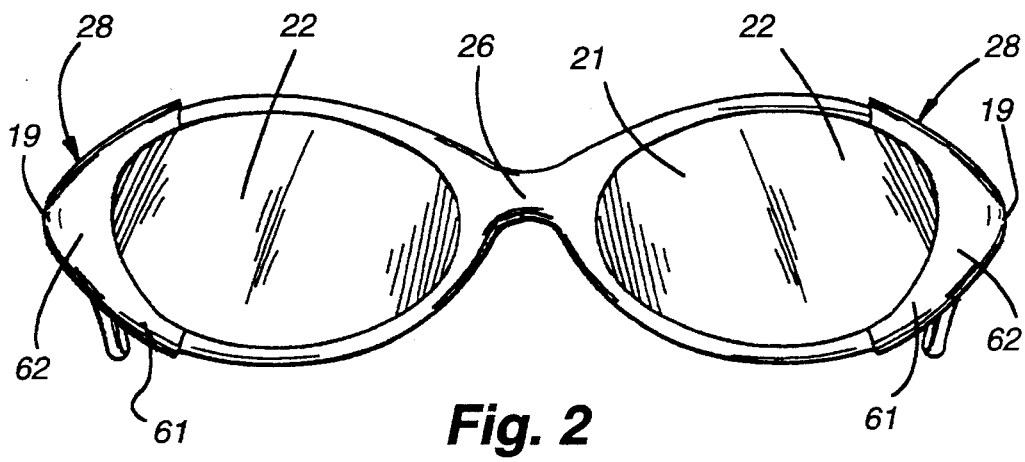
FIG. 2 is a front elevation view of the sunglasses with shields shown in FIG. 1.
Figure 3:
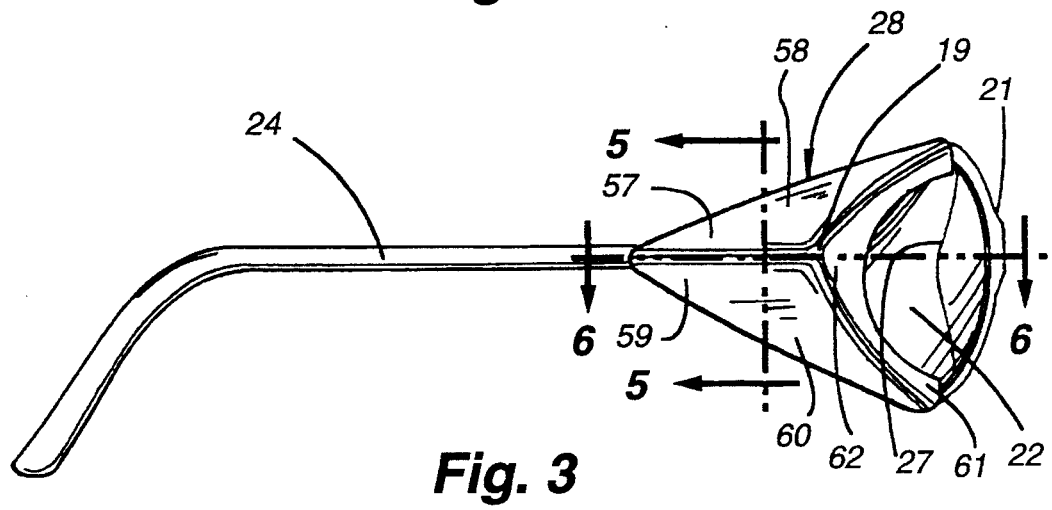
FIG. 3 is a side elevation view of the sunglasses with shields shown in FIG. 1, the opposite side being a mirror image thereof.
Figure 4:
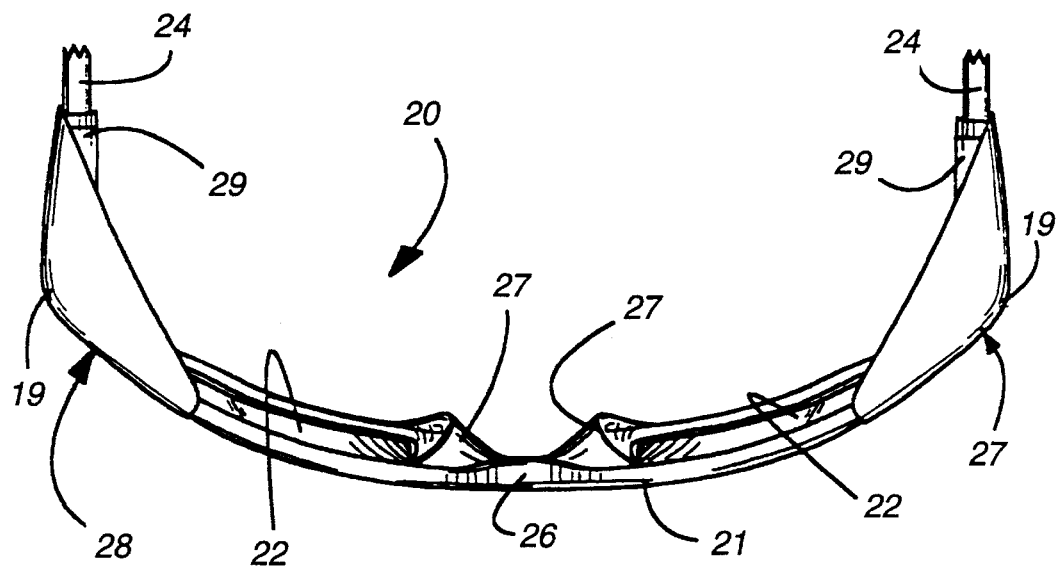
FIG. 4 is a top plan view of the sunglasses with shields shown in FIG. 1.
Figure 9:
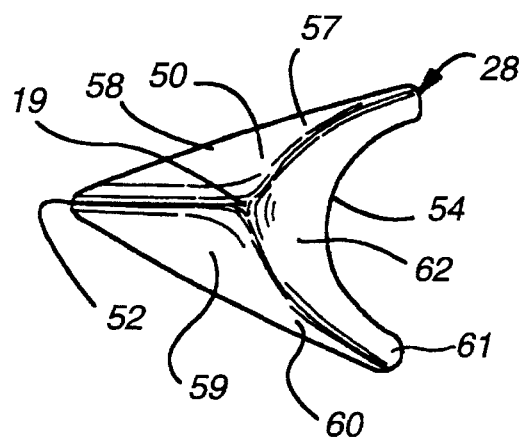
FIG. 9 is a side elevation view of a side shield as used on the eyeglasses shown in FIGS. 1 and 8.
Figure 10:
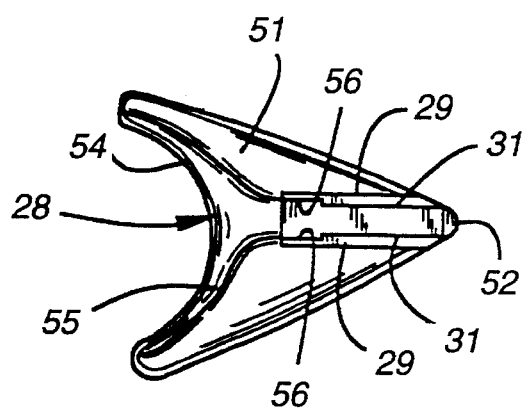
FIG. 10 is the opposite side elevation of the side shield shown in FIG. 9.
Figure 11:
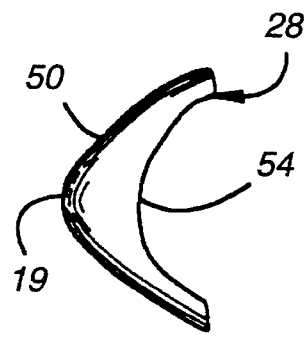
FIG. 11 is a front end elevation view of the side shield shown in FIG. 9.
Figure 13:
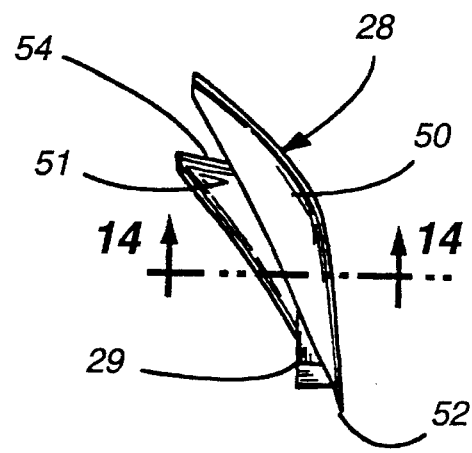
FIG. 13 is a top plan view of the side shield shown in FIG. 9.
Figure 12:
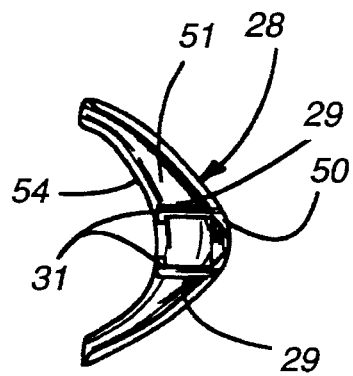
FIG. 12 is a rear end elevation view of the side shield shown in FIG. 9.
Figure 14:
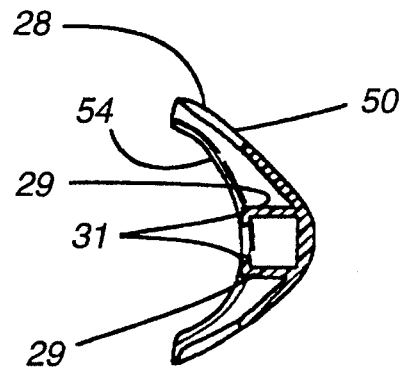
FIG. 14 is a section view taken substantially in the plane of line 14—14 on FIG. 13.

The shields 28, as shown in FIG. 5 and FIGS. 11-16, are each formed as a generally triangular panel or body with an outer convex surface 50 and an inner concave surface 51. The shield defines a rounded apex 52 opposite a concavely curved edge 54 which corresponds in curvature to the curvature of the hinge ends of the eyeglasses frame 21 as shown in FIG. 2. The inner surface 51 of the shield adjacent the curved edge 54 is flattened to define a ledge or shelf 55 adapted to receive and lie against the eyeglasses frame 21 and thereby provide a shield which, in appearance, is a continuation of the eyeglasses frame. As is shown in FIGS. 1, 3 and 9, each of the hollow, substantially pyramidal shields 28 includes a rounded tip 19, an upper shield panel 57 defining an upper shield surface 58, a substantially triangular lateral shield panel 59 defining a lateral shield surface 60, and forward facing panel 61 defining a forward facing surface 62. Referring to FIG. 1 it can be seen that the shields 28 serve to cover and shield not only the portions of the frame 21 and temples 24 adjacent the temple hinges 25 and the temple hinges 25 themselves, but further to cover and shield the user.

As described above, for mounting the shield on a temple the shield is formed with a pair of spaced apart integral ribs 29 defining therebetween a channel 30 for receiving a temple 24, as shown in FIG. 5. Inturned lips 31 on the channel ribs 29 wrap around or over the temple 24 to securely retain the shield thereon. At the forward end of the channel ribs, the lips 31 define recesses 56 to accommodate the temple hinge 35.

Because the shields are secured to the temples 24, when the temples 24 are folded back against the glasses, the shields likewise swing away from the frame enabling the user to store the eyeglasses in a suitable conventional case or holder.

While a certain illustrative embodiment of the present invention has been shown in the drawings and described above in detail, it should be understood that there is no intention to limit the invention to the specific form disclosed. On the contrary, the invention is to cover all modifications, alternative constructions, equivalents and uses falling within the spirit and scope of the invention as expressed in the appended claims.

I claim:

1. Sunglasses comprising a frame having rounded ends and mounting eyeglass lenses, a pair of temples, hinges mounting said temples on opposite ends of said frame, and a pair of substantially pyramidal shields each mounted on one of said temples adjacent said frame, said shields defining a rounded apex directed away from said hinges a concave edge adjacent to and adapted to receive and cover the frame end, an upper shield panel having an upper shield surface and a triangular lateral shield panel having a lateral shield surface adapted for covering and shielding portions of said frame and said temple adjacent said hinges when said sunglasses are worn by a user.

2. Sunglasses according to claim 1 wherein said upper shield surface and said lateral shield surface are each substantially triangular in shape.

3. Sunglasses according to claim 2 wherein said upper shield surface and said lateral shield surface are substantially convex.

4. Sunglasses according to claim 1 wherein said shields further define a forward facing shield surface.

5. Sunglasses comprising a frame mounting eyeglass lenses, a pair of temples, hinges mounting said temples on opposite ends of said frame, and substantially pyramidal shields removably mounted on said temples adjacent said hinges, said shields each comprising an upper shield panel and a generally triangular lateral shield panel having an outer convex surface and an inner concave surface and defining a rounded longitudinal apex opposite a concave edge leg, an inner ledge defined on said concave adjacent to said concave edge for receiving and covering a juxtaposed frame end, and a pair of spaced apart longitudinally extending ribs on said inner concave surface defining a channel for engaging a temple to support said shield thereon, and inturned lips on said ribs for releasably engaging said temple to retain said shields thereon, wherein said upper shield panel and said lateral shield panel are adapted for covering and protecting portions of said frame and said temple adjacent said hinges when said sunglasses are worn by a user.

6. Sunglasses according to claim 5 wherein said upper shield surface and said lateral shield surface are each substantially triangular in shape.

7. Sunglasses according to claim 6 wherein said upper shield surface and said lateral shield surface are substantially convex.

8. Sunglasses according to claim 5 wherein said shields further define a forward facing shield surface.

9. A removable shield for use with glasses having a frame having opposed, rounded ends and supporting a pair of eyeglass lenses, a pair of temples, hinges mounting said temples adjacent said opposed ends of said frame, said shields comprising a substantially pyramidal body having temple receiving channel for removably mounting said shields on said temples adjacent said hinges, said body including a rounded apex, an upper shield panel and a generally triangular lateral shield panel having an outer convex surface and an inner concave surface, wherein said upper shield panel and said lateral shield panel are adapted for covering and shielding portions of said frame and said temple adjacent said hinges when said glasses are worn by a user.

10. The shields according to claim 9, wherein said temple receiving channel for removably mounting said shields includes an inner ledge defined on said inner concave surface for receiving and covering a frame end, and a pair of spaced apart longitudinally extending ribs on said inner concave surface defining a channel for engaging a temple to support said shield thereon, and inturned lips on said ribs for releasably engaging said temple to retain said shields thereon.

11. The shields according to claim 9 wherein said upper shield surface and said lateral shield surface are each substantially triangular in shape.

12. Sunglasses according to claim 11 wherein said upper shield surface and said lateral shield surface are substantially convex.

13. Sunglasses according to claim 9 wherein said shields further define a forward facing shield surface.

* * * * *

UNITED STATES PATENT AND TRADEMARK OFFICE
CERTIFICATE OF CORRECTION

PATENT NO    : 5,608,469
DATED        : March 4, 1997
INVENTOR(S)  : Maurice Bollé

It is certified that error appears in the above-identified patent and that said Letters Patent is hereby corrected as shown below:

Col. 3,
Claim 1, line 1, delete "Sunglasses" and substitute therefore --Glasses--,
Col. 4, line 12, delete "sunglasses" and substitute therefore --glasses--;
Claim 2, line 1, delete "Sunglasses" and substitute therefore --Glasses--;
Claim 3, line 1, delete "Sunglasses" and substitute therefore --Glasses--;
Claim 4, line 1, delete "Sunglasses" and substitute therefore --Glasses--;
Claim 5, line 1, delete "Sunglasses" and substitute therefore --Glasses--;
Claim 6, line 1, delete "Sunglasses" and substitute therefore --Glasses--;
Claim 7, line 1, delete "Sunglasses" and substitute therefore --Glasses--;
Claim 8, line 1, delete "Sunglasses" and substitute therefore --Glasses--;
Claim 12, line 60, delete "Sunglasses" and substitute therefore --The shields--; and
Claim 13, line 63, delete "Sunglasses" and substitute therefore --The shields--.

Signed and Sealed this

Seventeenth Day of June, 1997

*Attest:*

BRUCE LEHMAN

*Attesting Officer*    Commissioner of Patents and Trademarks